United States Patent [19]

Vyas et al.

[11] Patent Number: 4,590,074
[45] Date of Patent: May 20, 1986

[54] BIS-AMIDINES

[75] Inventors: Dolatrai M. Vyas; Takushi Kaneko; Terrence W. Doyle, all of Fayetteville, N.Y.

[73] Assignee: Bristol-Myers Company, New York, N.Y.

[21] Appl. No.: 787,547

[22] Filed: Oct. 15, 1985

Related U.S. Application Data

[60] Division of Ser. No. 672,742, Nov. 19, 1984, which is a continuation-in-part of Ser. No. 492,903, May 9, 1983, Pat. No. 4,487,769, which is a continuation-in-part of Ser. No. 385,149, Jun. 4, 1982, abandoned.

[51] Int. Cl.$^4$ .................... A61K 31/40; C07D 403/04
[52] U.S. Cl. .................... 544/58.2; 548/422; 260/245.7; 544/58.5; 544/142; 546/199; 514/222; 514/234; 514/410

[58] Field of Search ............... 424/246, 248.54, 267, 424/274; 548/422; 260/245.7; 544/58.5, 142; 546/199

[56] References Cited

U.S. PATENT DOCUMENTS 3,660,578   5/1972   Tojuhata et al. .................. 514/410

OTHER PUBLICATIONS

Matsui et al., J. Antibiotics, vol. XXI (1968) pp. 189–198.

*Primary Examiner*—John Kight
*Assistant Examiner*—M. L. Moore
*Attorney, Agent, or Firm*—Robert E. Carnahan

[57] ABSTRACT

Symmetrical bis-amidine derivatives of mitomycin C may be converted to unsymmetrical bis-amidine analogs by reaction with secondary amines. The compounds are active anti-tumor agents in experimental animal tumors.

7 Claims, No Drawings

BIS-AMIDINES

CROSS-REFERENCE TO RELATED APPLICATIONS

This application is a divisional of Ser. No. 672,742, filed Nov. 19, 1984, which in turn is a continuation-in-part of copending application Ser. No. 492,903, filed May 9, 1983, now U.S. Pat. No. 4,487,769, which in turn is a continuation-in-part of application Ser. No. 385,149 filed June 4, 1982, now abandoned.

FIELD OF THE INVENTION

The present invention refers to mitomycin analogs containing two different amidino groups (Class 260 Subclass 326.24). These compounds are mitomycin C derivatives in which both the quinone amino group and the carbamido nitrogen atom are incorporated within an amidino substituent. These compounds are active antitumor substances against experimental animal tumors.

NOMENCLATURE

The systematic Chemical Abstracts name for mitomycin C is:
[1aR-(1a$\alpha$,8$\alpha$,8a$\beta$,8b$\alpha$)]-6-amino-8-[((aminocarbonyl)oxy)methyl]-1,1a,2,8,8a,8b-hexahydro-8a-methoxy-5-methyl-azirino[2',3',3,4]-pyrrolo[1,2-a]indole-4,7-dione according to which the azirinopyrroloindole ring system is numbered as follows:

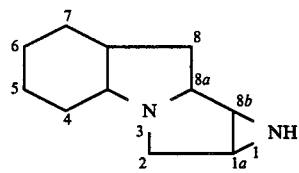

Chemical Abstracts

A trivial system of nomenclature which has found wide use in the mitomycin literature identifies the foregoing ring system including several of the characteristic substituents of the mitomycins as mitosane.

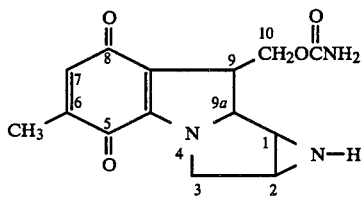

Mitosane

While this system is convenient and appropriate for a number of simple derivatives such as those bearing N-substituents on the azirino ring nitrogen atom or in the 7- or 9a-positions, it suffers from certain ambiguities and shortcomings for general use. With regard to the compounds of the present invention some of which have substituents on both the azirino ring nitrogen atom and on the side chain carbamoyl nitrogen atom, there is no conventional numbering to distinguish these positions. Therefore, we have chosen in the present specification to refer to the azirino nitrogen atom as $N^{1a}$ and the carbamoyl nitrogen atom as $N^{10}$ in using the mitosane nomenclature system. As to the stereochemical configuration of the products of this invention, it is intended when identifying them by the root name "mitosane" or by structural formula to identify the stereochemical configuration thereof as the same as that of mitomycin C.

DESCRIPTION OF THE PRIOR ART

Mitomycin C is an antibiotic which is produced by fermentation and is presently on sale under Food and Drug Administration approval in the therapy of disseminated adenocarcinoma of the stomach or pancreas in proven combinations with other approved chemotherapeutic agents and as palliative treatment when other modalities have failed (Mutamycin ® Bristol Laboratories, Syracuse, N.Y. 13201, Physician's Desk Reference 35th Edition, 1981, pp. 717 and 718). Mitomycin C and its production by fermentation are the subjects of U.S. Pat. No. 3,660,578 patented May 2, 1972 claiming priority from earlier applications including an application filed in Japan on Apr. 6, 1957.

The structures of mitomycins A, B, C, and of porfiromycin were first published by J. S. Webb et al. of Lederle Laboratories Division American Cyanamid Company, J. Amer. Chem. Soc. 94, 3185–3187 (1962).

Recently Shirahata et al., J. Am. Chem. Soc. 1983, 105, 7199–7200 have published convincing evidence as to the absolute configuration of mitomycin C on the basis of X-ray analysis of the $N^{1a}$-p-bromobenzoyl derivative thereof. The revised absolute configuration of mitomycin C is as shown in the following formula

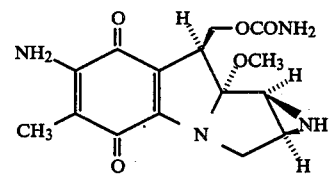

SUMMARY OF THE INVENTION

The present invention is concerned with a group of bis-amidino analogs of mitomycin C in which both the 7-amino nitrogen atom and the $N^{10}$-carbamoyl nitrogen atom are part of an amidino substituent. The two amidino groups of these bis-amidino compounds are different. Processes for the preparation of these compounds are included in the present invention. The compounds of the present invention conform to structural Formula I, which also includes compounds wherein the 7-amino nitrogen atom is incorporated within an amidino group, and the $N^{10}$-carbamoyl nitrogen atom is substituted by formyl.

The compounds of Formula I have utility as antitumor agents in that they inhibit the growth of malignant tumors in experimental animals. For this purpose they are administered systemically to a mammal bearing a tumor in a substantially non-toxic antitumor effective dose. The parenteral routes such as the intravenous route of administration are preferred. Disclosed herein are data comparing the present substances in vivo in various experimental animal tumor models with mitomycin C. Based upon these data the appropriate doses of the present substances can be estimated relative to the doses to mitomycin C employed in the treatment of various tumors. The compounds of Formula I are also antibiotics effective against Gram+ and Gram− bacteria.

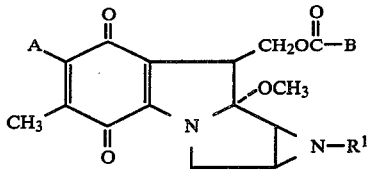

In Formula I, $R^1$ is hydrogen, lower alkyl, lower alkanoyl, benzoyl or substituted benzoyl wherein said substituent is lower alkyl, lower alkoxy, halo, amino, or nitro, A and B are different and are independently selected from the group having the formula

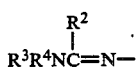

wherein $R^2$ is hydrogen, lower alkyl, phenyl, lower alkylphenyl, lower alkoxyphenyl, halophenyl, or aminophenyl, $R^3$ is lower alkyl, or lower alkoxy, $R^4$ is lower alkyl, or $R^3$ and $R^4$ together with the nitrogen atom to which they are attached constitute pyrrolidine, 2-, or 3-lower alkylpyrrolidine, piperidine, 2-, 3-, or 4-lower alkylpiperidine, 2,6-dilower alkylpiperidine, piperazine, 4-substituted piperazine wherein said 4-substituent is alkyl, or carbalkoxy each having 1 to 8 carbon atoms, phenyl, methylphenyl, methoxyphenyl, halophenyl, nitrophenyl, or benzyl, azepine, 2-, 3-, 4-, or 5-lower alkylazepine, morpholine, thiomorpholine, thiomorpholine-1-oxide, or thiomorpholine-1,1,-dioxide, or B is the amino formyl group.

DETAILED DESCRIPTION OF THE INVENTION

In application Ser. No. 492,903 (U.S. Pat. No. 4,487,769) it was disclosed that treatment of a bis-amidino compound similar to Formula I above in which A and B are each a dimethylaminomethyleneamino group with a primary amine in anhydrous methanol yielded a mitomycin C derivative similar to Formula I above in which A is a mono-substituted amino group corresponding to the amine reactant and B is the $NH_2$ group. Certain primary amines when employed in that process produce compounds similar to Formula I in which A is the amidino group of the starting material and B is the unsubstituted amino group. In other words, certain primary amines were capable of cleaving the $N^{10}$-amidino group, but not the $N^7$-amidino group of the compounds similar to Formula I in which A and B are identical amidino groups. We have now found that secondary amines react with such bis-amidino compounds to replace the amino portion of the B substituent with the amino group corresponding to the secondary amine used in the process. The following equation is illustrative.

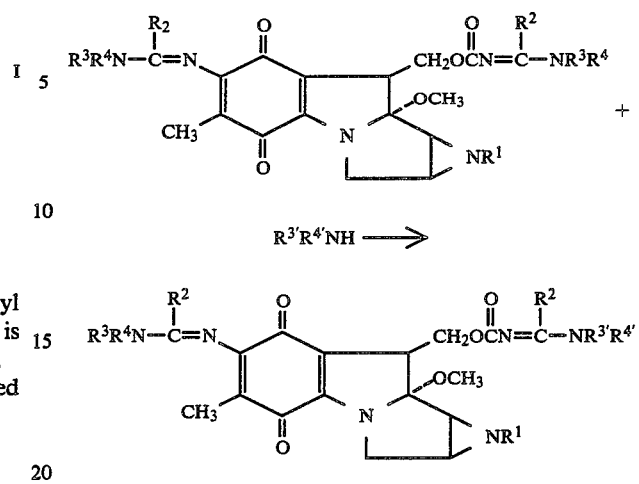

In the foregoing equation $R^1$, $R^2$, $R^3$, and $R^4$ have the definitions given above. $R^{3'}$ and $R^{4'}$ are also defined by the same group of terms used to define $R^3$ and $R^4$, but $R^{3'}$ and $R^{4'}$ represent different species with respect to $R^3$ and $R^4$ in any specific example.

The foregoing process is referred to as the amine exchange method. Substantially, any secondary amine may be employed in the process including alicyclic, cyclic, heteroalicyclic, and heteroaromatic secondary amines with the proviso that they contain no functional substituents which are sterically or chemically incompatible with the reaction conditions. Secondary amines having interfering functional groups may be employed if the functional group is derivatized by a conventional protecting group which may be removed after completion of the reaction. A variety of protecting groups and methods for their removal are known for groups such as hydroxyl, amino, and carboxyl. It is preferred that the carbon atoms attached to the nitrogen atom of the secondary amine reactant be methyl, methylene (—$CH_2$—), or methyne (—CH=) carbon atoms. Diisopropylamine has, for example, been found to be nonreactive in the process.

An anhydrous liquid organic compound is employed as reaction medium and any such substance may be employed so long as it is stable and substantially nonreactive to the reactants at the reaction temperature, and does not participtate in the reaction in any other deleterious way. Anhydrous methanol is the preferred reaction medium, but other media such as chloroform, methylene chloride, or other lower haloalkanes and alkanols may be employed. A reaction temperature in the range of from about −15° C. to about +50° C. is preferred. An excess of the amine reactant is preferably employed. By this is meant more than one molecular proportion relative to the bis-amidino mitomycin C derivative used as reactant.

The amide acetal method of Ser. No. 492,903 (U.S. Pat. No. 4,487,769) is also applicable to the preparation of the present compounds by using a compound of the following formula as reactant with the amide acetal according to the method of our prior application.

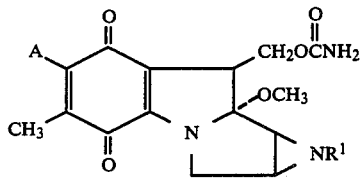

In the foregoing formula $R^1$ and A have the same meaning as given above. The entire disclosure of our prior application Ser. No. 492,903 is incorporated herein by reference and including particularly the discussion with respect to the amide acetal method and the identification of various amide acetals that may be employed in the process. More particularly, amide acetals having the following formula are employed.

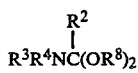

wherein $R^2$, $R^3$ and $R^4$ have the definitions given with respect to B in claim 1 and $R^8$ is independently lower alkyl, or cycloalkyl having up to 6 carbon atoms or together they are alkylene forming with the attached oxygen atoms and intervening carbon atom a cyclic structure having 5 or 6 ring members in solution in an anhydrous reaction compatible liquid organic reaction medium at 40° C. to 65° C. until the desired reaction product is formed.

In each of the foregoing processes it is desirable to monitor the course of the reaction by thin layer chromatography by means of which the starting material and product can be distinguished. The optimum reaction time is judged on the basis of disappearance of starting material, appearance of product, or a combination of each particularly in those instances wherein decomposition is a competing reaction.

SPECIFIC EMBODIMENTS

General Procedure

Amine Exchange Method: This method involves reaction of the symmetrical bis-amidino mitosane e.g.: Formula I wherein A and B are identical, with an excess of a secondary amine in anhydrous methanol at ambient temperature. Where possible, the progress of the reaction is monitored by thin layer chromatography. The reaction is terminated by evaporating the solvent and excess reagent under reduced pressure followed by removing the last traces under high vacuum. The resulting syrupy material is subsequently chromatographed to obtain the desired unsymmetrical bis-amidino mitosane which is then fully characterized. Flash chromatography on silica is appropriate, but when the conventional gravity flow method on a silica gel column is employed, degradation to the $N^{10}$-formyl compound sometimes occurs as is discussed more fully below.

Formamide Acetal Method: This method involves reaction of a 7-amidino mitosane e.g.: a compound similar to Formula I wherein B is $NH_2$ with an appropriate substituted formamide acetal in a methanol-chloroform mixture at ca. 55° C. for up to 72 hours. The progress of reaction is monitored by thin layer chromatography. After the reaction is complete, the reaction mixture is worked up in a similar manner to the above, and pure bis-amidine is obtained after neutral alumina column chromatography.

EXAMPLE 1

7-[(Dimethylamino)methylene]amino-$N^{10}$-(4-morpholinyl)methylene-9a-methoxymitosane

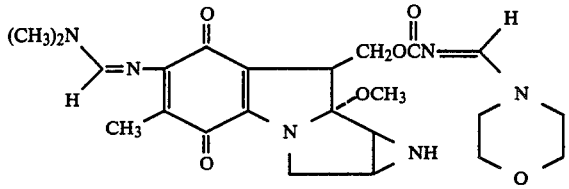

To a solution of 7-[(dimethylamino)methylene]amino-$N^{10}$-(dimethylamino)methylene-9a-methoxymitosane (485 mg, 1.09 mM) is anhydrous methanol (8 ml) was added morpholine (1 ml). After 3 hours the reaction mixture was evaporated on a rotovapor followed by high vacuum. The residue was flash chromatographed (short contact time) on a silica gel column using 5% MeOH in $CH_2Cl_2$. The less polar green material was collected and identified as the title compound (322 mg, 61%). An analytical sample was obtained by precipitating it from a solution of $CH_2Cl_2$ and ether with hexane to yield a green amorphous powder.

Anal Calc'd. for $C_{23}H_{30}N_6O_6$: C, 56.78; H, 6.22; N, 17.27. Found: C, 54.86; H, 6.38; N, 16.18.

IR(KBr, $\nu_{max}$, $Cm^{-1}$): 3440, 3305, 2920, 1675, 1620, 1540, 1445, 1375, 1310, 1275, 1060.

UV(MeOH, $\lambda_{max}$, nm): 386 and 248.

NMR(pyridine $d_5$, $\delta$): 1.80(br,m,1H), 2.12(s,3H), 2.74(m,1H), 2.84(s,3H), 2.88(s,3H), 3.20(s,3H), 3.20–3.84(m,12H), 4.04 (dd,1H,J=11,4 Hz), 4.39(d,1H,J=14 Hz), 5.04(t,1H), 5.43(dd, 1H,J=11,4 Hz), 7.83(s,1H), 8.38(s,1H).

EXAMPLE 2

7-[(Dimethylamino)methylene]amino-$N^{10}$-(1-piperidinylmethylene)-9a-methoxymitosane

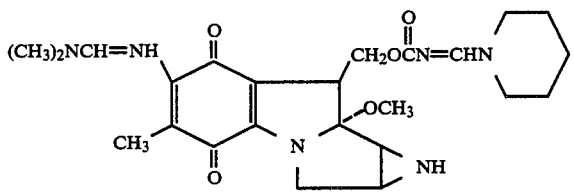

To a solution of 7-[(dimethylamino)methylene]amino-$N^{10}$-(dimethylamino)methylene-9a-methoxymitosane (520 mg, 1.17 mM) in anhydrous methanol was added piperidine (1 ml) and the reaction mixture stirred for 3.75 hours at ca. 22° C. The solvent and excess reagent were removed by first evaporating under reduced pressure on a rotavapor followed by high vacuum. The residue was flash chromatographed (short contact time) on silica gel column employing 5% MeOH in $CH_2Cl_2$ as the eluting solvent. The least polar green material was isolated as a green foam (131 mg, 23%) and was identified as the title compound. An analytical sample was obtained by precipitation from methylene chloride-ether-hexane solvent mixture.

Anal Calc'd. for $C_{19}H_{25}N_5O_5$: C, 59.49; H, 6.66; N, 17.34. Found: C, 58.56; H, 6.89; N, 16.20.

IR(KBr, $\nu_{max}$, $Cm^{-1}$): 3440, 2945, 1675, 1610, 1545, 1450, 1375, 1310, 1255, 1060.

UV(MeOH, $\lambda_{max}$, nm): 386 and 246.

NMR (pyridine d$_5$, $\delta$): 1.32(brs,6H), 1.92(m,1H), 2.12(s,3H), 2.76(brs,1H), 2.80(s,3H), 3.16(brs,2H), 3.20(s,3H), 3.60 (m,4H), 4.10(dd,1H,J=11,4 Hz), 4.44(d,1H,J=14 Hz), 5.08(t,1H), 5.50(dd,1H,J=11,4 Hz), 7.82(s,1H), 8.46(s,1H).

EXAMPLE 3

7-[(Dimethylamino)methylene]amino-N$^{10}$-(4-morpholinyl)methylene-9a-methoxymitosane To a solution of 7-[(dimethylamino)methylene]amino-9a-methoxymitosane (116 mg, 0.3 mM) in chloroform (5 ml) and methanol (1 ml) was added morpholine formamide dimethyl acetal (0.6 ml). The reaction mixture was stirred at ca. 55° C. (oil bath) for 48 hours. The progress of the reaction was monitored by silica gel thin layer chromatography (10% MeOH in CH$_2$Cl$_2$). At the completion of the reaction, almost all of the starting material (R$_f$=0.43) was converted to the major green material (R$_f$=0.57). The reaction mixture was evaporated on a rotavapor and the resulting oily residue was chromatographed on alumina column (Woelm, Grade III) using CH$_2$Cl$_2$ (50 ml), 1% MeOH in CH$_2$Cl$_2$ (50 ml), then 2% MeOH in CH$_2$Cl$_2$ as eluting solvents. The desired compound (96 mg, R$_f$=0.57) was obtained as an amorphous solid, whose NMR spectrum was identical to the compound described in Example 1.

The following compounds of Formula I wherein A is (CH$_3$)$_2$N—CH=N— and B has the meaning given below may be prepared by substituting the indicated amine for morpholine in Example 1.

| Example 1 Modification | |
|---|---|
| Amine Reactant | B of Product |
| Pyrrolidine | —N=CHN(pyrrolidinyl) |
| Thiomorpholine | —N=CHN(thiomorpholinyl, S) |
| Piperazine | —N=CHN(piperazinyl, NH) |
| Ethyl 1-piperazine-carboxylate | —N=CHN(piperazinyl, N—CO$_2$C$_2$H$_5$) |
| Azepine | —N=CHN(azepinyl) |
| Oxazepine | —N=CHN(oxazepinyl, O) |
| Thiazepine | —N=CHN(thiazepinyl, S) |
| 1,3-Diazine | —N=CHN(diazinyl, NH) |
| 1-Methylpiperazine | —N=CHN(piperazinyl, N—CH$_3$) |
| 1-Phenylpiperazine | —N=CHN(piperazinyl, N—C$_6$H$_5$) |

The following amide acetals may be substituted for morpholine formamide dimethyl acetal in the procedure of Example 3 to give the corresponding unsymmetrical bis-amidines of Formula I.

N,N-diisopropylformamide diethylacetal
N,N-Dimethylacetamide dimethylacetal
2,2-Dimethoxy-1-methylpyrrolidine

General Procedure for Preparing 7-amidino-N$^{10}$-formyl-9a-methoxymitosanes The procedure involves the reaction of a 7-amidino mitomycin C derivative with an excess of 4-morpholinyl formamide dimethyl acetal in chloroform at approximately 60° C. for 18 to 48 hours as is illustrated in Example 3. When the 7-amidino functionality is 4-morpholinyl methylene the N$^{10}$-formyl compound can be prepared directly from mitomycin C (see Example 4). Thin layer chromatography (silica gel, 10% MeOH in CH$_2$Cl$_2$) of the reaction mixture at the end of the reaction period reveals, that all of the starting material is converted to two faster moving green components. The excess acetal and solvent is removed by evaporation under reduced pressure followed by under high vacuum at approximately 60° C. When the resulting oily residue is chromatographed (drip method) on silica gel rather than alumina as specified in Example 3, degradation to a less polar green material occurs. This is isolated and characterized as the 7-amidino-N$^{10}$-formyl-9a-methoxymitosane compound. The N$^{10}$-formyl compounds are usually isolated as minor products by this method.

EXAMPLE 4

7-[(Morpholylamino)methylene]amino-$N^{10}$-formyl-9a-methoxymitosane

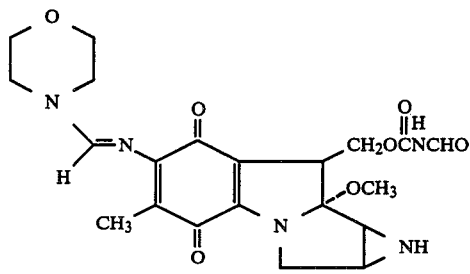

A suspension of mitomycin C (617 mg, 1.85 mM) in chloroform (30 ml) was heated with 4-morpholinyl formamide dimethyl acetal (19.5 ml) at 55° C. for 39 hours. The solvent and excess acetal was removed by evaporation on a rotovapor at 40° C. followed by under high vacuum until approximately 5 ml of oily residue was left. The oily residue was chromatographed on silica gel (40 gm) column packed, employing the slurry method and using $CH_2Cl_2$. The column was eluted with $CH_2Cl_2$ (200 ml), 2% MeOH in $CH_2Cl_2$ (350 ml) and 5% MeOH in $CH_2Cl_2$ (200 ml). Fractions containing the least polar green material were pooled and concentrated. This material was rechromatographed on silica gel column packed with 4% MeOH in $CH_2Cl_2$. Elution with the same solvent, collection, and evaporation of the first green band afforded the title compound as a dark green amorphous solid (50 mg).

Anal. Calc'd for $C_{19}H_{23}N_5O_6$: C, 54.90; H, 5.48; N, 15.24. Found: C, 52.00; H, 5.44; N, 13.55.

IR (KBr, $\nu_{max}$, cm$^{-1}$): 3420, 3280, 2910, 1755, 1700, 1620, 1540, 1440, 1380, 1305, 1205, 1100, 1060, 1020.

UV (MeOH, $\lambda_{max}$, nm): 381 and 229.

NMR (pyridine d$_5$, δ): 2.10(s,3H), 2.14(t,1H,J=8 Hz), 2.84 (brs,1H), 3.08(brs,1H), 3.26(s,3H), 3.39(brs,2H), 3.50-3.80 (m,7H), 4.05(dd,1H,J=13,3 Hz), 4.42(d,1H,J=13 Hz), 5.15(t,1H, J=13 Hz), 4.44(dd,1H,J=13,3 Hz), 7.95(s,1H), 9.45(2,1H), 13.1(brs,1H).

EXAMPLE 5

7-[(Dimethylamino)methylene]amino-$N^{10}$-formyl-9a-methoxymitosane

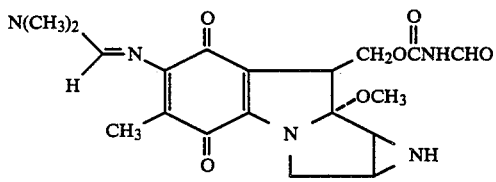

To a solution of 7-[(dimethylamino)methylene]amino-9a-methoxymitosane 379 mg, 0.97 mM) in chloroform was added 4-morpholinyl formamide dimethyl acetal (3.5 ml). The reaction mixture was heated at 55° C. for 18 hours. The process of the reaction was monitored by thin layer chromatography (silica gel, 10% MeOH in $CH_2Cl_2$. The reaction mixture was evaporated on a rotovapor at 40° C. followed by under high vacuum at 60° C. The oily residue was chromatographed on silica gel column packed using $CH_2Cl_2$. Elution with $CH_2Cl_2$ (100 ml), 5% MeOH in $CH_2Cl_2$ (300 ml) and 10% MeOH in $CH_2Cl_2$ (200 ml) afforded two green colored syrups. The faster moving component was rechromatographed on silica gel column packed with 5% MeOH in $CH_2Cl_2$. Elution with the same solvent (250 ml) followed by with 10% MeOH in $CH_2Cl_2$ (250 ml) afforded 40 mg of the less polar amorphous solid green material which was characterized as the title compound.

Anal. Calc'd for $C_{19}H_{23}N_5O_6$: C, 54.63; H, 5.51; N, 16.77. Found: C, 54.35; H, 5.30; N, 16.15.

IR (KBr), $\nu_{max}$, cm$^{-1}$): 3460, 3300, 2930, 1765, 1710, 1630, 1550, 1440, 1380, 1310, 1210, 1105, 1060

UV (MeOH, $\lambda_{max}$, nm): 387 and 233.

NMR (pyridine d$_5$, δ): 2.14(2,3H), 2.26(t,1H,J=8 Hz), 2.82(s,4H), 2.90(s,3H), 3.05(brs,1H), 3.28(s,3H), 3.63 (d,1H,J=13 Hz), 4.04(dd,1H,J=13,3 Hz), 4.45(d,1H,J=13 Hz), 5.18(t,1H,J=13 Hz), 5.43(dd,1H,J=13,3 Hz), 7.90(s,1H), 9.45(s,1H), 13.14(brs,1H).

Activity Against P-388 Murine Leukemia

The following table contains the results of laboratory tests with CDF$_1$ male mice implanted intraperitoneally with a tumor inoculum of 10$^6$ ascites cells of P-388 murine leukemia and treated with various doses of either a test compound of Formula I or mitomycin C. The compounds were administered by intraperitoneal injection. Groups of six mice were used for each dosage level and they were treated with a single dose of the compound on day one only. A group of ten saline treated control mice was included in each series of experiments. The mitomycin C treated groups were included as a positive control. A 30 day protocol was employed with the mean survival time in days being determined for each group of mice and the number of survivors at the end of the 30 day period being noted. The mice were weighed before treatment and again on day six. The change in weight was taken as a measure of drug toxicity. Mice weighing 20 grams each were employed and a loss in weight of up to approximately 2 grams was not considered excessive. The results were determined in terms of % T/C which is the ratio of the mean survival time of the treated group to the mean survival time of the saline treated control group times 100. The mean survival time for saline treated control animals was nine days. The "maximum effect" in the following table is expressed as % T/C and the dose giving that effect is given. The values in parenthesis are the values obtained with mitomycin C as the positive control in the same experiment. Thus a measure of the relative activity of the present substances to mitomycin C can be estimated. A minimum effect in terms of % T/C was considered to be 125. The minimum effective dose reported in the following table is that dose giving a % T/C of approximately 125. The two values given in each instance in the "average weight change" column are respectively the average weight change per mouse at the maximum effective dose and at the minimum effective dose.

| | Inhibition of P-388 Murine Leukemia | | | |
|---|---|---|---|---|
| Compound (Example No.) | Maximum Effect | | Minimum effective dose | Average weight change[2] |
| | % T/C | dose[1] | | |
| 1 | 222 (172) | 6.4 (3.2) | 0.1 | −0.4; +1.7 |
| 2 | 194 (172) | 6.4 (3.2) | 0.4 | +0.2; +0.6 |
| 4 | 175 (270) | 3.2 (4.8) | <0.4 | −0.5; +0.3 |

-continued

| Compound (Example No.) | Inhibition of P-388 Murine Leukemia | | | Average weight change[2] |
|---|---|---|---|---|
| | Maximum Effect | | Minimum effective dose | |
| | % T/C | dose[1] | | |
| 5 | 170 (270) | 3.2 (4.8) | 0.4 | −1.4; +1.3 |

[1]mg/kg of body weight
[2]grams per mouse, days 1-6, at maximum and minimum effective doses Compounds 1 and 2 were similarly found to provide maximal survival increases greater than mitomycin C in mice bearing B16 melanoma implants.

What is claimed is:

1. The process for the preparation of a compound having the formula $$\text{[structure: quinone-indole with A, CH}_3\text{, O, O, CH}_2\text{OC-B, OCH}_3\text{, N, N-R}^1\text{]}$$

wherein
   $R^1$ is hydrogen, lower alkyl, lower alkanoyl, benzoyl or substituted benzoyl wherein said substituent is lower alkyl, lower alkoxy, halo, amino, or nitro, and
   A and B are different and are independently selected from the amidino group having the formula $$R^3R^4NC=N-\underset{R^2}{\overset{|}{\phantom{C}}}$$

wherein
   $R^2$ is hydrogen, lower alkyl, phenyl, lower alkylphenyl, lower alkoxyphenyl, halophenyl, or aminophenyl,
   $R^3$ is lower alkyl, or lower alkoxy,
   $R^4$ is lower alkyl, or
   $R^3$ and $R^4$ together with the nitrogen atom to which they are attached constitute pyrrolidine, 2-, or 3- lower alkylpyrrolidine, piperidine, 2-, 3-, or 4- lower alkylpiperidine, 2,6-dilower alkylpiperidine, piperazine, 4-substituted piperazine wherein said 4-substituent is alkyl, or carbalkoxy each having 1 to 8 carbon atoms, phenyl, methylphenyl, methoxyphenyl, halophenyl, nitrophenyl, or benzyl, azepine, 2-, 3-, 4-, or 5-lower alkylazepine, morpholine, thiomorpholine, thiomorpholine-1-oxide, or thiomorpholine-1,1-dioxide, or
   B is the amino formyl group (NHCHO)
which comprises contacting a compound of the formula $$\text{[structure: quinone-indole with A, CH}_3\text{, O, O, CH}_2\text{OC-A, OCH}_3\text{, N, N-R}^1\text{]}$$

wherein $R^1$ and A have the above definitions with a secondary amine of the formula $R^3R^4NH$ wherein $R^3$ and $R^4$ are as defined above with respect to B at a temperature of from 20° C. to 60° C. for a sufficient period of time to produce the desired compound.

2. The process of claim 1 wherein an anhydrous reaction compatible liquid organic reaction medium is employed.

3. The process of claim 2 wherein said reaction medium comprises methanol, chloroform, methylene chloride or other lower haloalkane.

4. The process for preparing a compound having the formula $$\text{[structure: quinone-indole with A, CH}_3\text{, O, O, CH}_2\text{OC-B, OCH}_3\text{, N, N-R}^1\text{]}$$

wherein
   $R^1$ is hydrogen, lower alkyl, lower alkanoyl, benzoyl or substituted benzoyl wherein said substituent is lower alkyl, lower alkoxy, halo, amino, or nitro, and
   A and B are different and are independently selected from the amidino group having the formula $$R^3R^4NC=N-\underset{R^2}{\overset{|}{\phantom{C}}}$$

wherein
   $R^2$ is hydrogen, lower alkyl, phenyl, lower alkylphenyl, lower alkoxyphenyl, halophenyl, or aminophenyl,
   $R^3$ is lower alkyl, or lower alkoxy,
   $R^4$ is lower alkyl, or
   $R^3$ and $R^4$ together with the nitrogen atom to which they are attached constitute pyrrolidine, 2-, or 3- lower alkylpyrrolidine, piperidine, 2-, 3-, or 4- lower alkylpiperidine, 2,6-dilower alkylpiperidine, piperazine, 4-substituted piperazine wherein said 4-substituent is alkyl, or carbalkoxy each having 1 to 8 carbon atoms, phenyl, methylphenyl, methoxyphenyl, halophenyl, nitrophenyl, or benzyl, azepine, 2-, 3-, 4-, or 5-lower alkylazepine, morpholine, thiomorpholine, thiomorpholine-1-oxide, or thiomorpholine-1,1-dioxide, or
   B is the amino formyl group (NHCHO)
which comprises reacting a compound having the formula $$\text{[structure: quinone-indole with A, CH}_3\text{, O, O, CH}_2\text{OCNH}_2\text{, OCH}_3\text{, N, NR}^1\text{]}$$

with an amide acetal of the formula $$R^3R^4NC(OR^8)_2\underset{R^2}{\overset{|}{\phantom{C}}}$$

wherein A, $R^1$, $R^2$, $R^3$ and $R^4$ have the definitions given above and $R^8$ is independently lower alkyl, or cycloalkyl having up to 6 carbon atoms or together they are alkylene forming with the attached oxygen atoms and intervening carbon atom a cyclic structure having 5 or 6 ring members in solution in an anhydrous reaction compatible liquid organic reaction medium at 40° C. to 65° C. until the desired reaction product is formed.

5. The process of claim 4 wherein said reaction medium is chloroform.

6. The process of claim 4 wherein the reaction medium is a mixture of a halogenated lower aliphatic hydrocarbon and a lower alkanol.

7. The process of claim 4 wherein said reaction medium is a mixture of chloroform and methanol.

* * * * *